US012758312B2

(12) United States Patent
Hancock et al.

(10) Patent No.: US 12,758,312 B2
(45) Date of Patent: Oct. 13, 2026

(54) ELECTROSURGICAL APPARATUS FOR CUTTING AND COAGULATION

(71) Applicant: Creo Medical Limited, Chepstow (GB)

(72) Inventors: Christopher Paul Hancock, Chepstow (GB); Malcolm White, Chepstow (GB)

(73) Assignee: Creo Medical Limited, Chepstow (GB)

( * ) Notice: Subject to any disclaimer, the term of this patent is extended or adjusted under 35 U.S.C. 154(b) by 709 days.

(21) Appl. No.: 18/019,023

(22) PCT Filed: Jul. 13, 2021

(86) PCT No.: PCT/EP2021/069513
§ 371 (c)(1),
(2) Date: Jan. 31, 2023

(87) PCT Pub. No.: WO2022/028826
PCT Pub. Date: Feb. 10, 2022

(65) Prior Publication Data

US 2023/0310077 A1 Oct. 5, 2023

(30) Foreign Application Priority Data

Aug. 3, 2020 (GB) ...................................... 2012034

(51) Int. Cl.
*A61B 18/12* (2006.01)
*A61B 18/18* (2006.01)
*A61B 18/00* (2006.01)

(52) U.S. Cl.
CPC ............................... *A61B 18/1815* (2013.01); *A61B 2018/00404* (2013.01); *A61B 2018/00589* (2013.01);
(Continued)

(58) Field of Classification Search
CPC ..... A61B 18/12; A61B 18/18; A61B 18/1815; A61B 18/14; A61B 18/1492;
(Continued)

(56) References Cited

U.S. PATENT DOCUMENTS

| | | | | |
|---|---|---|---|---|
| 10,299,850 B2 | 5/2019 | Amoah et al. | | |
| 2007/0225699 A1* | 9/2007 | Goble | .................... A61B 18/12 | 606/34 |

(Continued)

FOREIGN PATENT DOCUMENTS

| | | | |
|---|---|---|---|
| GB | 2 506 377 | A | 4/2014 |
| JP | 2002-537938 | A | 11/2002 |

(Continued)

OTHER PUBLICATIONS

International Search Report and Written Opinion mailed Oct. 27, 2021, in connection with International Application No. PCT/EP2021/069513.

(Continued)

*Primary Examiner* — Thomas A Giuliani
(74) *Attorney, Agent, or Firm* — Wolf, Greenfield & Sacks, P.C.

(57) ABSTRACT

The invention relates to an electrosurgical apparatus for cutting and coagulating biological tissue. In particular, the present invention provides an electrosurgical generator arranged to generate radiofrequency (RF) electromagnetic (EM) energy and microwave frequency EM energy; wherein the electrosurgical generator is operable in each of a coagulation mode and a cutting mode, wherein in the coagulation mode the electrosurgical generator is arranged to deliver the RF EM energy and the microwave EM energy simultaneously in a coagulation composite waveform comprising a dominant microwave signal and a supplementary RF signal, and wherein in the cutting mode the electrosurgical generator is arranged to deliver the RF EM energy and the microwave EM energy simultaneously in a cutting composite waveform comprising a dominant RF signal and a supplementary microwave signal.

12 Claims, 4 Drawing Sheets

(52) U.S. Cl.
CPC ............... *A61B 2018/00601* (2013.01); *A61B 2018/00607* (2013.01); *A61B 2018/00702* (2013.01); *A61B 2018/00767* (2013.01); *A61B 2018/1823* (2013.01)

(58) Field of Classification Search
CPC ...... A61B 18/1206; A61B 2018/00589; A61B 2018/00601; A61B 2018/00607; A61B 2018/00702; A61B 2018/1823; A61B 2018/00827; A61B 2018/00994; A61B 2018/122; A61B 2018/00785; A61B 2018/00869; A61B 2018/00892; A61B 2018/1861; A61B 2018/128; A61B 2018/1876; A61B 2017/00141; A61B 2017/00154
USPC ........ 606/32–34, 37, 41–42, 45, 49; 607/98, 607/99, 101, 113, 115, 116, 156
See application file for complete search history.

(56) References Cited

U.S. PATENT DOCUMENTS

| | | | | |
|---|---|---|---|---|
| 2013/0267943 | A1* | 10/2013 | Hancock ............... | H05B 6/806 606/33 |
| 2013/0289557 | A1 | 10/2013 | Hancock et al. | |
| 2015/0238257 | A1* | 8/2015 | Hancock ............ | A61B 18/1206 606/33 |
| 2016/0374752 | A1* | 12/2016 | Hancock ............ | A61B 18/1815 606/33 |
| 2019/0125442 | A1* | 5/2019 | Hancock ............ | A61B 18/1492 |

FOREIGN PATENT DOCUMENTS

| | | | |
|---|---|---|---|
| JP | 2014-511190 | A | 5/2014 |
| JP | 2015-530172 | A | 10/2015 |
| JP | 2019-517843 | A | 6/2019 |
| WO | WO 00/53112 | A2 | 9/2000 |
| WO | WO 2015/087051 | A1 | 6/2015 |

OTHER PUBLICATIONS

International Preliminary Report on Patentability, Chapter II, mailed Nov. 3, 2022, in connection with International Application No. PCT/EP2021/069513.
British Search Report dated Feb. 2, 2021, in connection with British Application No. GB 2012034.1.
Written Opinion dated Jun. 20, 2022, in connection with International Application No. PCT/EP2021/069513.
Aditya et al., Vessel Sealing Device Using Microwave and High Frequency Current. IEEE Journal of Electromagnetics, RF and Microwaves in Medicine and Biology. Jul. 24, 2020;5(2):108-114.
Japanese Office Action, mailed Oct. 15, 2024, in connection with Japanese Application No. 2023-503064, with English translation.

* cited by examiner

ELECTROSURGICAL APPARATUS FOR CUTTING AND COAGULATION

RELATED APPLICATIONS

This Application is a national stage filing under 35 U.S.C. 371 of International Patent Application Serial No. PCT/EP2021/0695134, filed Jul. 13, 2021, entitled "ELECTROSURGICAL APPARATUS FOR CUTTING AND COAGULATION" which claims priority to United Kingdom application number 2012034.1, filed Aug. 3, 2020, each of which is herein incorporated by reference in its entirety.

FIELD OF THE INVENTION

The invention relates to an electrosurgical apparatus for cutting and coagulating biological tissue. In particular, it relates to composite radiofrequency (RF) and microwave frequency electromagnetic (EM) energy waveforms for delivery from an electrosurgical generator to a bipolar electrode configuration at a distal end of an electrosurgical instrument. The composite waveforms are arranged to promote effective cutting and coagulation.

BACKGROUND TO THE INVENTION

Surgical resection is a means of removing sections of organs from within the human or animal body. Such organs may be highly vascular. When tissue is cut (divided or transected) small blood vessels called arterioles are damaged or ruptured. Initial bleeding is followed by a coagulation cascade where the blood is turned into a clot in an attempt to plug the bleeding point. During an operation, it is desirable for a patient to lose as little blood as possible, so various devices have been developed in an attempt to provide blood-free cutting. For endoscopic procedures, it is also undesirable for a bleed to occur and not to be dealt with as quickly as possible, or in an expedient manner, since the blood flow may obscure the operator's vision, which may lead to the procedure needing to be terminated and another method used instead, e.g. open surgery.

Electrosurgical generators are pervasive throughout hospital operating theatres, for use in open and laparoscopic procedures, and are also increasingly present in endoscopy suites. In endoscopic procedures the electrosurgical accessory is typically inserted through a lumen inside an endoscope. Considered against the equivalent access channel for laparoscopic surgery, such a lumen is comparatively narrow in bore and greater in length.

Instead of a sharp blade, it is known to use radiofrequency (RF) energy to cut biological tissue. The method of cutting using RF energy operates using the principle that as an electric current passes through a tissue matrix (aided by the ionic contents of the cells and the intercellular electrolytes), the impedance to the flow of electrons across the tissue generates heat. When an RF voltage is applied to the tissue matrix, enough heat is generated within the cells to vaporise the water content of the tissue. As a result of this increasing desiccation, particularly adjacent to the RF emitting region of the instrument which has the highest current density of the entire current path through tissue, the tissue adjacent to the cut pole of the instrument loses direct contact with the blade. The applied voltage then appears almost entirely across this void which ionises as a result, forming a plasma (which may also be referred to herein as a microplasma), which has a very high volume resistivity compared to tissue. This differentiation is important as it focusses the applied energy to the plasma that completed the electrical circuit between the cut pole of the instrument and the tissue. Any volatile material entering the plasma slowly enough is vaporised and the perception is therefore of a tissue dissecting plasma.

GB 2 486 343 discloses a control system for an electrosurgical apparatus which delivers both RF and microwave energy to treat biological tissue. The energy delivery profile of both RF energy and microwave energy delivered to a probe is set based on sampled voltage and current information of RF energy conveyed to the probe and sampled forward and reflected power information for the microwave energy conveyed to and from the probe.

FIG. 3 shows a schematic diagram of an electrosurgical apparatus 400 as set out in GB 2 486 343. The apparatus comprises a RF channel and a microwave channel. The RF channel contains components for generating and controlling an RF frequency electromagnetic signal at a power level suitable for treating (e.g. cutting or desiccating) biological tissue. The microwave channel contains components for generating and controlling a microwave frequency electromagnetic signal at a power level suitable for treating (e.g. coagulating or ablating) biological tissue.

The microwave channel has a microwave frequency source 402 followed by a power splitter 424 (e.g. a 3 dB power splitter), which divides the signal from the source 402 into two branches. One branch from the power splitter 424 forms a microwave channel, which has a power control module comprising a variable attenuator 404 controlled by controller 406 via control signal $V_{10}$ and a signal modulator 408 controlled by controller 406 via control signal $V_{11}$, and an amplifier module comprising drive amplifier 410 and power amplifier 412 for generating forward microwave EM radiation for delivery from a probe 420 at a power level suitable for treatment. After the amplifier module, the microwave channel continues with a microwave signal coupling module (which forms part of a microwave signal detector) comprising a circulator 416 connected to deliver microwave EM energy from the source to the probe along a path between its first and second ports, a forward coupler 414 at the first port of the circulator 416, and a reflected coupler 418 at the third port of the circulator 416. After passing through the reflected coupler, the microwave EM energy from the third port is absorbed in a power dump load 422. The microwave signal coupling module also includes a switch 415 operated by the controller 406 via control signal $V_{12}$ for connecting either the forward coupled signal or the reflected coupled signal to a heterodyne receiver for detection.

The other branch from the power splitter 424 forms a measurement channel. The measurement channel bypasses the amplifying line-up on the microwave channel, and hence is arranged to deliver a low power signal from the probe. In this embodiment, a primary channel selection switch 426 controlled by the controller 406 via control signal $V_{13}$ is operable to select a signal from either the microwave channel or the measurement channel to deliver to the probe. A high band pass filter 427 is connected between the primary channel selection switch 426 and the probe 420 to protect the microwave signal generator from low frequency RF signals.

The measurement channel includes components arranged to detect the phase and magnitude of power reflected from the probe, which may yield information about the material e.g. biological tissue present at the distal end of the probe. The measurement channel comprises a circulator 428 connected to deliver microwave EM energy from the source 402 to the probe along a path between its first and second ports. A reflected signal returned from the probe is directed into the third port of the circulator 428. The circulator 428 is used to provide isolation between the forward signal and the reflected signal to facilitate accurate measurement. However, as the circulator does not provide complete isolation between its first and third ports, i.e. some of the forward signal may break through to the third port and interfere with the reflected signal, a carrier cancellation circuit is used that injects a portion of the forward signal (from forward coupler 430) back into the signal coming out of the third port (via injection coupler 432). The carrier cancellation circuit include a phase adjustor 434 to ensure that the injected portion is 180° out of phase with any signal that breaks through into the third port from the first port in order to cancel it out. The carrier cancellation circuit also include a signal attenuator 436 to ensure that the magnitude of the injected portion is the same as any breakthrough signal.

To compensate for any drift in the forward signal, a forward coupler 438 is provided on the measurement channel. The coupled output of the forward coupler 438 and the reflected signal from the third port of the circulator 428 are connected to respective input terminal of a switch 440, which is operated by the controller 406 via control signal $V_{14}$ to connect either the coupled forward signal or the reflected signal to a heterodyne receiver for detection.

The output of the switch 440 (i.e. the output from the measurement channel) and the output of the switch 415 (i.e. the output from the microwave channel) are connect to a respective input terminal of a secondary channel selection switch 442, which is operable by the controller 406 via control signal $V_{15}$ in conjunction with the primary channel selection switch to ensure that the output of the measurement channel is connected to the heterodyne receiver when the measurement channel is supplying energy to the probe and that the output of the microwave channel is connected to the heterodyne receiver when the microwave channel is supplying energy to the probe.

The heterodyne receiver is used to extract the phase and magnitude information from the signal output by the secondary channel selection switch 442. A single heterodyne receiver is shown in this system, but a double heterodyne receiver (containing two local oscillators and mixers) to mix the source frequency down twice before the signal enters the controller may be used if necessary. The heterodyne receiver comprises a local oscillator 444 and a mixer 448 for mixing down the signal output by the secondary channel selection switch 442. The frequency of the local oscillator signal is selected so that the output from the mixer 448 is at an intermediate frequency suitable to be received in the controller 406. Band pass filters 446, 450 are provided to protect the local oscillator 444 and the controller 406 from the high frequency microwave signals.

The controller 406 receives the output of the heterodyne receiver and determines (e.g. extracts) from it information indicative of phase and magnitude of the forward and/or reflected signals on the microwave or measurement channel. This information can be used to control the delivery of high power microwave EM radiation on the microwave channel or high power RF EM radiation on the RF channel. A user may interact with the controller 406 via a user interface 452, as discussed above.

The RF channel shown in FIG. 3 comprises an RF frequency source 454 connected to a gate driver 456 that is controlled by the controller 406 via control signal $V_{16}$. The gate driver 456 supplies an operation signal for an RF amplifier 458, which is a half-bridge arrangement. The drain voltage of the half-bridge arrangement is controllable via a variable DC supply 460. An output transformer 462 transfers the generated RF signal on to a line for delivery to the probe 420. A low pass, band pass, band stop or notch filter 464 is connected on that line to protect the RF signal generator from high frequency microwave signals.

A current transformer 466 is connected on the RF channel to measure the current delivered to the tissue load. A potential divider 468 (which may be tapped off the output transformer) is used to measure the voltage. The output signals from the potential divider 468 and current transformer 466 (i.e. voltage outputs indicative of voltage and current) are connected directly to the controller 406 after conditioning by respective buffer amplifiers 470, 472 and voltage clamping Zener diodes 474, 476, 478, 480 (shown as signals B and C in FIG. 3).

To derive phase information, the voltage and current signals (B and C) are also connected to a phase comparator 482 (e.g. an EXOR gate) whose output voltage is integrated by RC circuit 484 to produce a voltage output (shown as A in FIG. 3) that is proportional to the phase difference between the voltage and current waveforms. This voltage output (signal A) is connected directly to the controller 406.

The microwave/measurement channel and RF channel are connected to a signal combiner 114, which conveys both types of signal separately or simultaneously along cable assembly to the probe 420, from which it is delivered (e.g. radiated) into the biological tissue of a patient.

A waveguide isolator (not shown) may be provided at the junction between the microwave channel and signal combiner. The waveguide isolator may be configured to perform three functions: (i) permit the passage of very high microwave power (e.g. greater than 10 W); (ii) block the passage of RF power; and (iii) provide a high withstanding voltage (e.g. greater than 10 kV). A capacitive structure (also known as a DC break) may also be provided at (e.g. within) or adjacent the waveguide isolator. The purpose of the capacitive structure is to reduce capacitive coupling across the isolation barrier.

The present invention provides improvements to an electrosurgical apparatus, in particular increasing the effectiveness of cutting and coagulation operations.

SUMMARY OF THE INVENTION

At its most general, the invention provides a coagulation waveform and a cutting waveform which each comprise simultaneous delivery of radiofrequency (RF) and microwave frequency electromagnetic (EM) signals. It has been found that by supplementing a dominant signal of a first frequency with a supplementary frequency of a second frequency, the cutting or coagulation effects of the delivered EM energy are greatly improved.

According to a first aspect of the invention, there is provided an electrosurgical generator arranged to generate radiofrequency (RF) electromagnetic (EM) energy and microwave frequency EM energy; wherein the electrosurgical generator is operable in each of a coagulation mode and a cutting mode, wherein in the coagulation mode the electrosurgical generator is arranged to deliver the RF EM energy and the microwave EM energy simultaneously in a coagulation composite waveform comprising a dominant microwave signal and a supplementary RF signal, and wherein in the cutting mode the electrosurgical generator is arranged to deliver the RF EM energy and the microwave EM energy simultaneously in a cutting composite waveform comprising a dominant RF signal and a supplementary microwave signal. A dominant signal should be understood as an EM signal which has higher power than that of a supplementary signal, and a supplementary signal should be understood as an EM signal which has a lower power than that of a dominant signal. For this reason, the dominant signal may be referred to as a high-power signal, and the supplementary signal may be referred to as a low-power signal.

In a coagulation mode, by providing a coagulation composite waveform comprising a dominant microwave signal and a supplementary RF signal which are delivered simultaneously, it has been found that a greater total power is delivered to biological tissue than when using a microwave signal alone.

This results in an increase in the maximum bleeding volume rate that can be coagulated, and so the coagulation composite waveform gives the ability to deal with more severe bleeding than can be stopped using microwave power alone, or by interleaving (e.g. alternating) microwave and RF signals.

Preferably, in the coagulation mode, the supplementary RF signal is delivered at a low power level, which may be a power level which is low relative to the dominant microwave signal, which is suitable to result in localised heating of biological tissue but which is not suitable for generating microplasmas, which may result in tissue cutting. By delivering a supplementary RF signal in this way, energy delivery at the distal tip of an electrosurgical instrument may be increased for improved coagulation by the coagulation composite waveform. Advantageously, in the coagulation mode, the dominant microwave signal is delivered at a high power level, which may be a power level which is high relative to the supplementary RF signal, which is suitable to promote coagulation of biological tissue. For example, the power level of the RF signal may be controlled using a feedback circuit built into an RF circuit in the generator, wherein the feedback may be used to control current, power and voltage to limit the voltage of the RF signal so that the current and power fall within predetermined safe limits (i.e. limits which do not result in the generation of microplasmas).

For example, in the coagulation composite waveform, the dominant microwave signal may be delivered at a power level of 10 W or less. The dominant microwave signal may preferably be delivered as a continuous wave (CW) signal.

For example, in the coagulation composite waveform the supplementary RF signal may be delivered having an RMS voltage in the range of 75 to 100 V, and a power level of less than 10 W, for example 3W or less, such as 2 W. The supplementary RF signal may be delivered as either a CW signal or as a pulsed signal, for example a pulsed signal having a duty cycle of at least 10%.

In a cutting mode, by providing a cutting composite waveform comprising a dominant RF signal and a supplementary microwave signal which are delivered simultaneously, it has been found that the supplementary microwave signal increases the power in a microplasma formed at the distal tip of an electrosurgical instrument, and so improves cutting performance. In addition, the microwave signal may couple to biological tissue, resulting in some denaturing and thereby changing the impedance of the biological tissue to the dominant RF signal which also provides improved cutting performance.

Preferably, in the cutting mode, the dominant RF signal is provided at a high power level, which may be a power level which is high relative to the power level of the supplementary microwave signal, which is suitable for generating microplasmas for cutting tissue at the distal end of an electrosurgical instrument. Advantageously, in the cutting mode, the supplementary microwave signal is delivered at a low power level, which may be a power level which is low relative to the power level of the dominant RF signal, which is suitable for denaturing and desiccating biological tissue. For example, the power level of the microwave signal may be dependent on the power level of the dominant RF signal to ensure that the simultaneous delivery of the dominant RF signal and the supplementary microwave signal is suitable for denaturing and desiccating biological tissue in the region of the cut. In the cutting mode, the microwave signal power is less than the RF signal power, but may be provided at its own predetermined or pre-set maximum level, with the level of the RF signal contributing to cutting tissue. In some embodiments, the dominant RF signal and the supplementary microwave signal may be switched synchronously.

Preferably, in the cutting composite waveform the dominant RF signal may be delivered having an RMS voltage of at least 300 V, and a power level of at least 30 W, such a 40 W or more. The dominant RF signal may be delivered as a CW signal or as a pulsed signal.

In the cutting composite waveform, the supplementary microwave signal may be delivered as a continuous wave signal, or as a pulsed signal, for example a pulsed signal having a duty cycle of at least 10%. Preferably, the microwave signal may be delivered at a power of 10 W or less.

In one example of a cutting composite waveform, the dominant RF signal and the supplementary microwave signal may be delivered simultaneously until microplasma have been initiated, whereupon the dominant RF signal may be turned off and the microplasma sustained by the microwave signal alone. For example, the microplasma may be sustained with a microwave signal being delivered at the same power or at a higher power than the supplementary microwave signal.

According to a second aspect of the invention, there is provided an electrosurgical apparatus comprising: an electrosurgical generator according to the first aspect of the invention; an electrosurgical instrument having a distal tip assembly for delivering RF EM energy and microwave EM energy into biological tissue; and a feed cable connected to deliver the RF EM energy and the microwave frequency EM energy from the electrosurgical generator to the electrosurgical instrument.

According to a third aspect of the invention, there is provided a method of delivering radiofrequency (RF) electromagnetic (EM) energy and microwave frequency EM energy from an electrosurgical generator to electrosurgical instrument that has a distal tip assembly for delivering RF EM energy and microwave EM energy into biological tissue, the method comprising operating the generator to deliver the RF EM energy and the microwave frequency EM energy simultaneously in either of a coagulation composite waveform for promoting haemostasis in biological tissue or a cutting composite waveform for cutting biological tissue, wherein: the coagulation composite waveform comprises a dominant microwave frequency signal and a supplementary RF signal which are delivered simultaneously, and the cutting composite waveform comprises a dominant RF signal and a supplementary microwave frequency signal which are delivered simultaneously.

Herein, the term “inner” means radially closer to the centre (e.g. axis) of the coaxial cable, probe tip, and/or applicator. The term “outer” means radially further from the centre (axis) of the coaxial cable, probe tip, and/or applicator.

The term “conductive” is used here to mean electrically conductive, unless the context dictates otherwise.

Herein, the terms "proximal" and "distal" refers to the ends of the applicator. In use, the proximal end is closer to a generator for providing the RF and/or microwave energy, whereas the distal end is further from the generator.

In this specification "microwave" may be used broadly to indicate a frequency range of 400 MHz to 100 GHz, but preferably in the range 1 GHz to 60 GHz. Specific frequencies that have been considered are: 915 MHz, 2.45 GHz, 3.3 GHz, 5.8 GHz, 10 GHz, 14.5 GHz, and 25 GHz. In contrast, this specification uses "radiofrequency" or "RF" to indicate a frequency range that is at least three orders of magnitude lower, e.g. up to 300 MHz, preferably 10 kHz to 1 MHz, and most preferably 400 kHz. The microwave frequency may be adjusted to enable the microwave energy delivered to be optimised. For example, a probe tip may be designed to operate at a certain frequency (e.g. 900 MHz), but in use the most efficient frequency may be different (e.g. between 902 and 928 MHz).

The term "electrosurgical" is used in relation to an instrument, apparatus, or tool which is used during surgery and which utilises radiofrequency and/or microwave frequency electromagnetic (EM) energy.

BRIEF DESCRIPTION OF THE DRAWINGS

Features of the invention are now explained in the detailed description of examples of the invention given below with reference to the accompanying drawings, in which.

DETAILED DESCRIPTION; FURTHER OPTIONS AND PREFERENCES

This invention broadly relates to composite waveforms comprising simultaneous signals of both radiofrequency (RF) and microwave frequency electromagnetic (EM) energy for enhanced cutting and coagulation.

Figure 1:
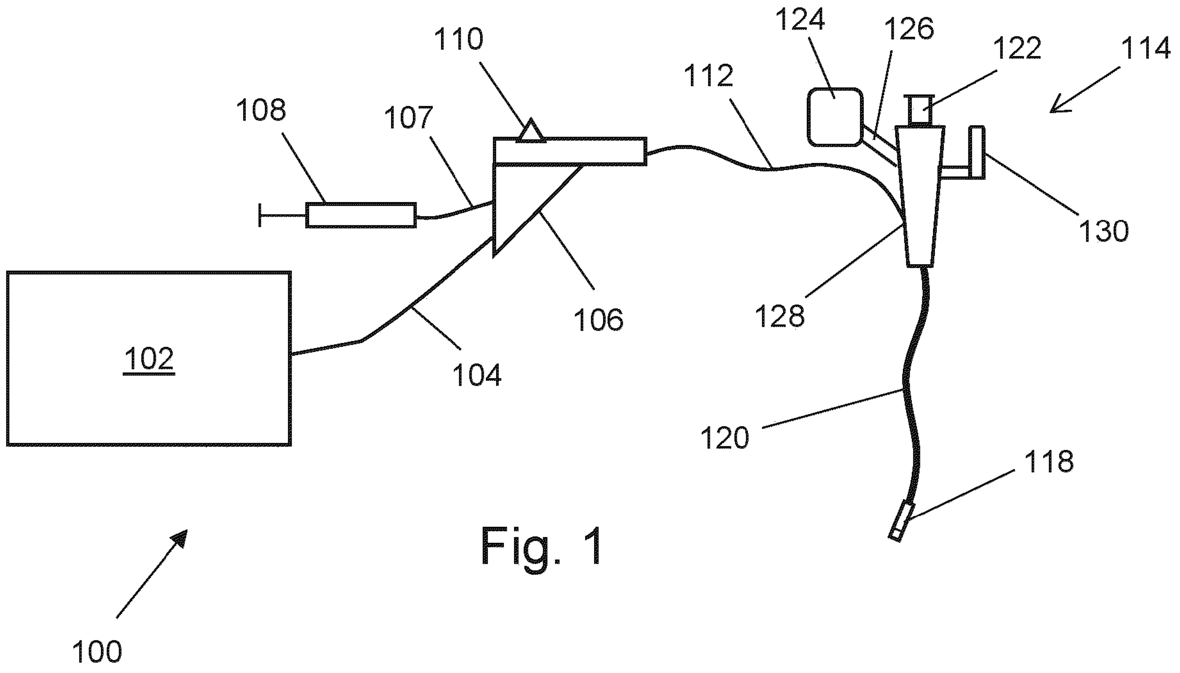
FIG. 1 is a schematic view of an electrosurgery system for use in an embodiment of the invention.
Figure 3:
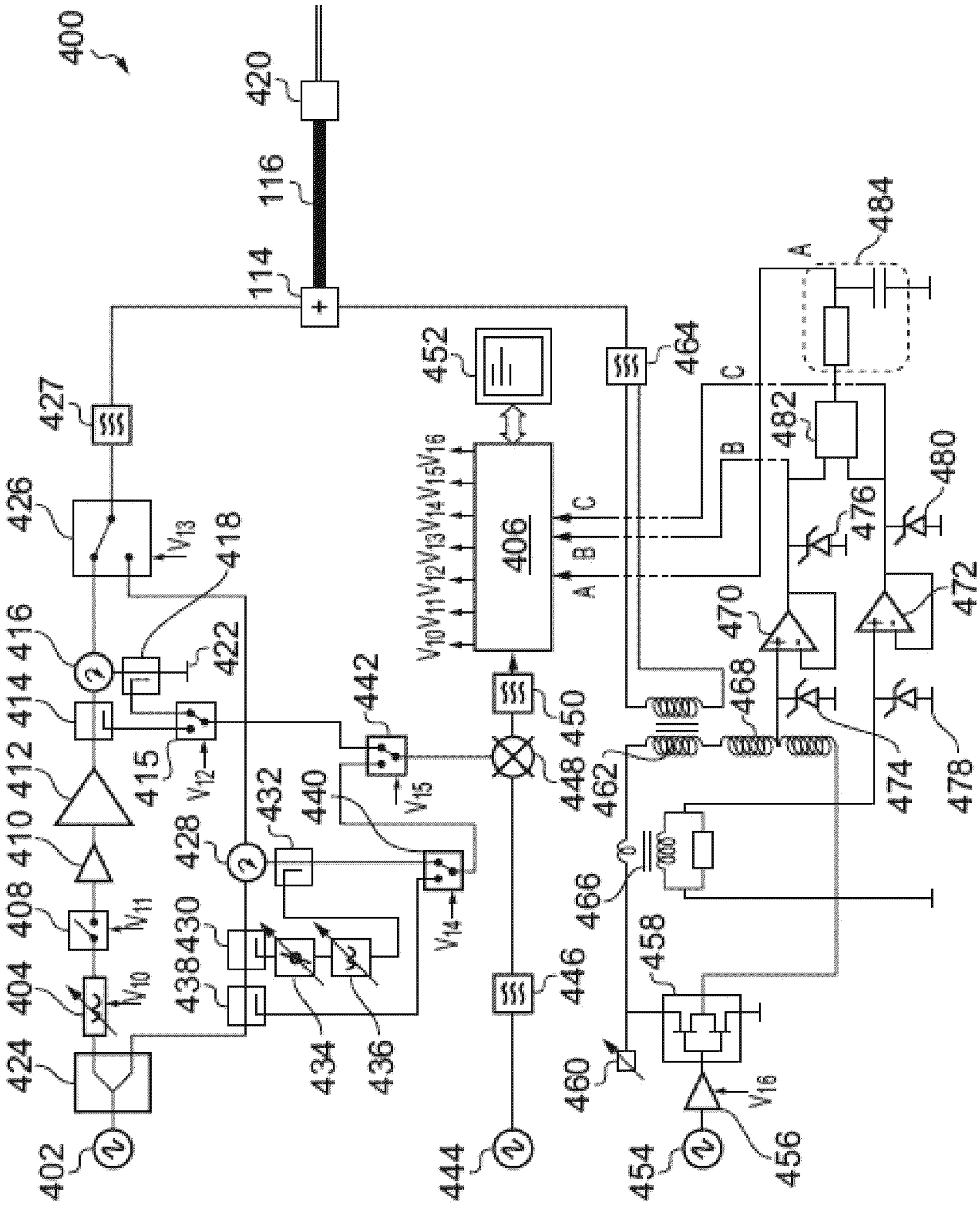
Fig. 3 (Prior Art)
FIG. 3 is an overall schematic diagram of an electrosurgical apparatus in which the present invention may be used.

FIG. 1 is a schematic diagram of a complete electrosurgery system 100 that is capable of selectively supplying to the distal end of an invasive electrosurgical instrument any or all of RF energy, microwave energy and fluid, e.g. saline or hyaluronic acid. The system 100 comprises a generator 102 for controllable supplying RF electromagnetic (EM) energy and/or microwave frequency EM energy. The generator 102 may be as shown in the electrosurgical apparatus 400 discussed above with reference to FIG. 3. The generator 102 may be arranged to monitor reflected signals received back from the instrument in order to determine an appropriate signal to be conveyed to the instrument. For example, the generator 102 may be arranged to calculate an impedance seen at the distal end of the instrument in order to determine an optimal delivery power level.

The generator 102 is connected to an interface joint 106 by an interface cable 104. The interface joint 106 is also connected to receive a fluid supply 107 from a fluid delivery device 108, such as a syringe, although this need not be essential. If needed, the interface joint 106 can house an instrument control mechanism that is operable by sliding a trigger 110, e.g. to control longitudinal (back and forth) movement of one or more control wires or push rods (not shown). If there is a plurality of control wires, there may be multiple sliding triggers on the interface joint to provide full control. The function of the interface joint 106 is to combine the inputs from the generator 102, fluid delivery device 108 and instrument control mechanism into a single flexible shaft 112, which extends from the distal end of the interface joint 106. The internal configuration of the interface joint 106 is discussed in more detail below.

The flexible shaft 112 is insertable through the entire length of an instrument (working) channel of a surgical scoping device 114, such as an endoscope, gastroscope, laparoscope or the like. A torque transfer unit is mounted on a proximal length of the shaft 112 between the interface joint 106 and surgical scoping device 114. The torque transfer unit engages the shaft to permit it to be rotated within the instrument channel of the surgical scoping device 114.

The flexible shaft 112 has an electrosurgical instrument tip 118 that is shaped to pass through the instrument channel of the surgical scoping device 114 and protrude (e.g. inside the patient) at the distal end of the endoscope's tube. The instrument tip includes an active tip for delivering composite waveforms of RF EM energy and microwave EM energy into biological tissue, and a retractable hypodermic needle for delivering fluid. These combined technologies provide for cutting and destroying unwanted tissue and the ability to seal blood vessels around the targeted area. Through use of the retractable hypodermic needle, the surgeon is able to inject saline and/or hyaluronic acid with added marker dye between tissues layers in order to distend and mark the position of a lesion to be treated. The injection of fluid in this manner lifts and separates the tissue layers making it both easier to resect around the lesion and plane through the submucosal layer, reducing the risk of bowel wall perforation and unnecessary thermal damage to the muscle layer.

As discussed in more detail below, the instrument tip 118 further includes a protective hull positioned under the active tip to assist a tissue planing type resection action, again helping to protect against inadvertent perforation and ensure viability of the remaining tissue, which in turn facilitates more rapid healing and post operation recovery.

The structure of the instrument tip discussed below may be particularly designed for use with a conventional steerable flexible endoscope having a working channel with an internal diameters of at least 3.3 mm and a channel length of between 60 cm and 170 cm. As such the majority of the comparatively small diameter (less than 3 mm) instrument is housed within the lumen of a much larger and predominantly polymer insulating device, i.e. the flexible endoscope channel, which typically has an outer diameter of 11 mm to 13 mm. In practice, only 15 mm to 25 mm of the distal assembly protrudes from the distal end of the endoscope channel, in order not to block the field of view or adversely affect camera focusing. The protruding part of the distal assembly is the only portion of the instrument that ever makes direct contact with the patient.

At the proximal end of the endoscope working channel, which is typically held 50 cm to 80 cm from the patient, the flexible shaft 112 emerges from the working channel port and extends a further 30 cm to 100 cm to the interface joint 106. In use, the interface joint 106 is typically held by a gloved assistant throughout the procedure. The interface joint 106 is designed and manufactured from polymer materials in such a way as to provide primary and secondary electrical insulation with extended creepage and clearance distances. The interface cable 104 is connected to the generator 102 using a QN-type coaxial interface, and to the interface joint using a QMA-type coaxial interface, which is designed to allow continuous clockwise or counter clockwise rotation. This permits the interface joint 106 to rotate with the torque transfer unit under the control of the user. The assistant supports the interface joint 106 throughout the procedure in order to assist the user with sympathetic instrument rotation, needle control and fluid injection.

Figure 2:
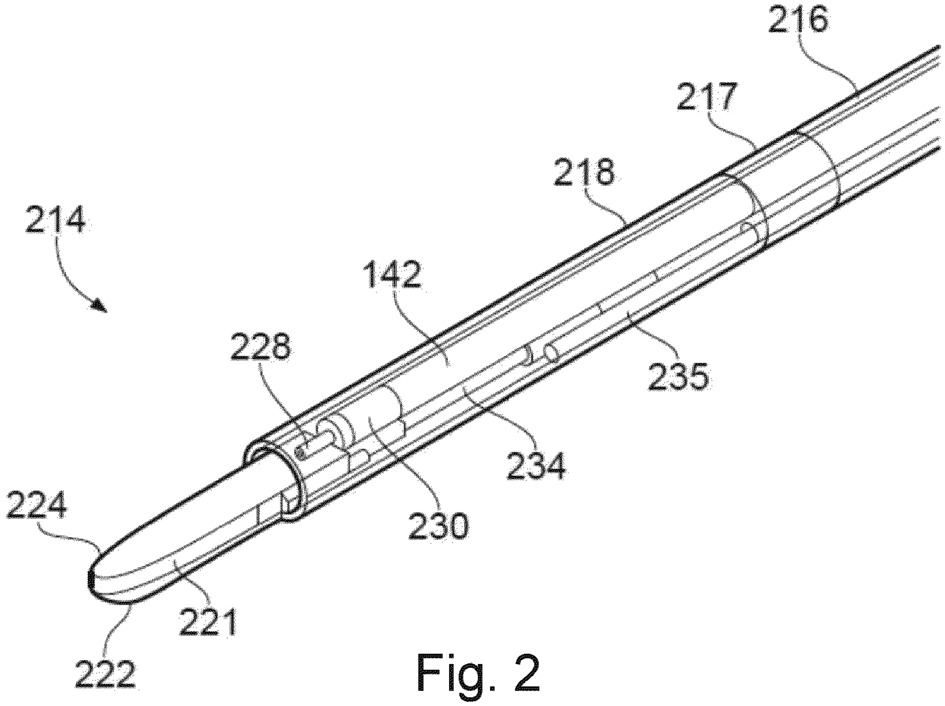
FIG. 2 is a partly transparent perspective view of a distal end of an electrosurgical instrument that is suitable for use in the present invention.

FIG. 2 shows a transparent view of a distal end assembly 214 (sometimes referred to as an instrument tip) of an electrosurgical instrument that may be used in embodiments of the invention. The instrument tip may be provided as set out in GB 2 565 575. A tubular portion 218, support sleeve 217 and cannula tube 216 are shown as transparent so that the inner components are visible. Parts of a protective hull 222 within the tubular portion 218 are omitted to show how an electrically conductive element 230 fits over an outer conductor.

The distal end assembly 214 is mounted at the distal end of an outer cannula tube 216 of a flexible shaft, e.g. which correspond to the flexible shaft 112 discussed above with reference to FIG. 1. The cannula tube 216 forms a flexible sleeve defining a lumen for transporting fluid to the instrument tip, the instrument tip being secured at its distal end. In order to provide a torque transfer function, the outer cannula tube 216 is formed of a braided tube, e.g. comprising a braided wire (e.g. stainless steel) wrap mounted between a radially inner polymer layer and a radially outer polymer layer, wherein the polymer may be e.g. Pebax®.

In this embodiment, the outer cannula tube 216 is connected at its distal end to an unbraided tubular portion 218, which may be a flexible conduit. The tubular portion 218 may be formed from any suitable polymer material, e.g. Pebax® or the like. The tubular portion 218 may have an axial length (i.e. length in line with the shaft axis equal to or greater than 1 mm. This may ensure that a safe distance is introduced between the end of the braiding and the proximal edge of the distal end assembly 214 in order to avoid any risk of heating of the braid as a result of capacitive conductance during use of microwave energy. This arrangement may also prevent the two plates of the planar transmission line or the two conductors in the coaxial transmission line from becoming shorted or connected together.

The tubular portion 218 may be referred to as a 'soft tip' 218. The soft tip 218 may in some embodiments be an additional length of polymer tube which is bonded to the distal end of the sleeve or cannula tube 216. The bonding may use any suitable adhesive, e.g. epoxy or the like. A support tube 217 may be mounted over the junction between the tubular portion 218 and cannula tube 216 to reinforce the joint by providing additional mechanical strength. The support tube 217 may be a short section of polymer tubing within which the both the tubular portion 218 and the cannula tube 216 are secured, e.g. by bonding. The support tube 217 may be flexible and/or may have a length selected to ensure that it does not adversely affect the flexibility of the shaft.

The junction of the tubular portion 218, cannula tube 216 and support tube 217 may also be captured within a heat shrink sleeve (not shown) to provide further structural strength at the distal end of the shaft.

The braiding within the cannula tube 216 enables torque applied to the proximal end of the shaft to be transformed into rotational movement of the instrument tip. For convenience, some of the accompanying illustrations show the tubular portion 218 and cannula tube 216 as transparent. In practical embodiments, the shaft may be opaque.

A distal end of the tubular portion 218 is arranged to fit over a corresponding proximal part 220 of a protective hull 222. The protective hull is formed from a metallic material having low friction with biological tissue, e.g. stainless steel, and is shaped to perform a number of functions, i.e.

- mount the distal end assembly 214 on the flexible shaft,
- provide a protective undersurface for an active tip structure that delivers energy into surrounding biological tissue,
- provide a protective housing and supporting frame for a retractable needle, and
- locate the active tip structure relative to the coaxial cable during assembly and subsequent use.

The distal end assembly 214 includes an active tip 224, which is a planar piece of dielectric material 221 (e.g. alumina) having conductive layers (e.g. layers of metallisation) on its upper and lower surfaces. The conductive layers are each electrically connected to a respective one of an inner conductor 228 and an outer conductor of a coaxial cable 142 that is conveyed by the cannula tube 216. At a distal end of the coaxial cable 142, its outer sheath is removed to expose a length of the outer conductor. The inner conductor 228 of the coaxial cable extends beyond the distal end of the outer conductor. The coaxial cable 142 and the active tip 224 are mounted relative to one another so that the protruding part of the inner conductor 228 lies on a first conductive layer of the active tip, while the outer conductor is brought into electrical connection with a second conductive layer via the protective hull 222, as discussed below. The first conductive layer is isolated from the outer conductor and the second conductive layer is isolated from the inner conductor 228.

The conductive layers may be formed from high melting point conductors, e.g. W or Ti. However, in one example, to facilitate the use of solder in the electrical connection between the inner and outer conductors of the coaxial cable 142 and the active tip 224, lower melting point conductors may be deposited at proximal regions on the conductive layers where the electrical connections are made. The lower melting point conductors may be silver (Ag) or gold (Au).

The distal end of the active tip 224 is curved to avoid presenting sharp corners within the patient.

The outer conductor is electrically connected to a lower conductive layer on the underside of the active tip 224 via the protective hull 222. A proximal end of the protective hull 222 is formed with a U-shaped channel for receiving and supporting a distal end of the coaxial feed cable 142. The distal end assembly is configured so that the exposed portion of the outer conductor sits in the U-shaped channel. An electrically conductive element 230, such as a sleeve or collar, is used to crimp the exposed portion of the outer conductor. The compression caused by the crimp means that the coaxial cable deforms in the region where it is received by the protective hull 222. For example, the portion of the coaxial cable where the outer conductor is exposed may have an oval cross-section, whereby it abuts and forms a robust electrical contact with the sides of the U-shaped channel 248. The crimped outer conductor may thus be retained by the hull via an interference fit.

To complete the electrical connection between the outer conductor and a lower conductive layer on the active tip 224, the protective hull 222 is electrically coupled to the lower conductive layer, e.g. by soldering. In this embodiment, a solder preform is provided for this purpose. The solder preform is shaped to be receivable within a recess formed in an upper surface of the protective hull 222. In one example, the recess is rectangular, and the solder preform has a corresponding shape, but any suitable shape may be used. The recess is set back from the edges of the protective hull in a manner that ensures solder is only present between the lower surface of the active tip 224 and the protective hull 222, i.e. it does not flow to the side edges of the active tip 224. When assembled, the solder preform may be aligned with a region on the lower surface of the active tip 224 that is coated in a lower melting point conductor as discussed above (e.g. gold). A suitable flex (not shown) may be provided with the solder preform when the components are assembled to facilitate the soldering process. The soldering process itself may be induction soldering. The induction soldering effect may be confined to a region of the active tip 224 and protective hull 222 at the solder preform.

The above configuration is advantageous because the protective hull 222 retains all of (i) the active tip 224, (ii) the solder preform, and (iii) the coaxial cable 142 in a fixed spatial relationship which ensures accurate and repeatable assembly.

The distal end assembly further comprises a needle guide that is retained within a recess formed in the undersurface of the protective hull 222. The needle guide is a hollow tube (e.g. a ferrule), e.g. made of polyimide, within which a hypodermic needle 234 is slidably mounted. The needle 234 is in fluid communication with the internal volume of the cannula tube 216 in order to receive liquid present therein for delivery to the treatment site.

After the distal end assembly 214 is assembled, it may be secured within the distal end of the tubular portion 218 by an interference fit and an adhesive (e.g. epoxy). The adhesive may also form a plug for the distal end of the tubular portion 218 to provide a fluid tight seal that means the only exit for fluid introduced at the interface joint is through the needle 234. Similarly, the junction (e.g. soldered joint) between the inner conductor 228 and an upper conductive layer may have a protective cover that may be formed from a suitable adhesive (e.g. epoxy). The protective cover may strengthen the connection between the protective hull 222 and active tip 224, while also forming an end plug for the tubular portion 218, i.e. a fluid tight seal that means the only exit for fluid introduced at the interface joint is through the needle.

In use the active tip 224 makes an intimate contact with the patient. The needle 234 can be extended beyond the distal end of the active tip 224 and retracted to a position back inside a guide tube via control of the slider mechanism on the interface joint which acts on a control wire 235 to deploy and retract the needle 234. In its extended position, the needle is used to inject fluid for the purpose of locally distending and/or marking tissue. The conductive layers on the active tip 224 form bi-polar electrodes for delivering RF and/or microwave electromagnetic energy.

The needle guide 232 extends back inside and proximal to the distal assembly to provide extended creepage clearance to ensure RF/microwave activation only occurs across the distal tip region of the active tip 224.

The distal end of the hull is shaped to permit the active tip 224 to overhang it by around 0.2 mm around the distal edge except at the distal tip. The surface that contacts the underside of the active tip therefore has a maximum width of 2 mm, which narrows to 1.6 mm in an intermediate portion before tapering to its distal tip in a distal portion. The distal tip may be a single radiused curve, e.g. having a radius of 0.2 mm.

FIGS. 4 to 7 show schematic representations of waveforms for delivery from an electrosurgical instrument such as that discussed above in an embodiment of the invention. Each waveform is depicted as a graph having time along the x-axis and signal strength along the y-axis.

Figure 4:
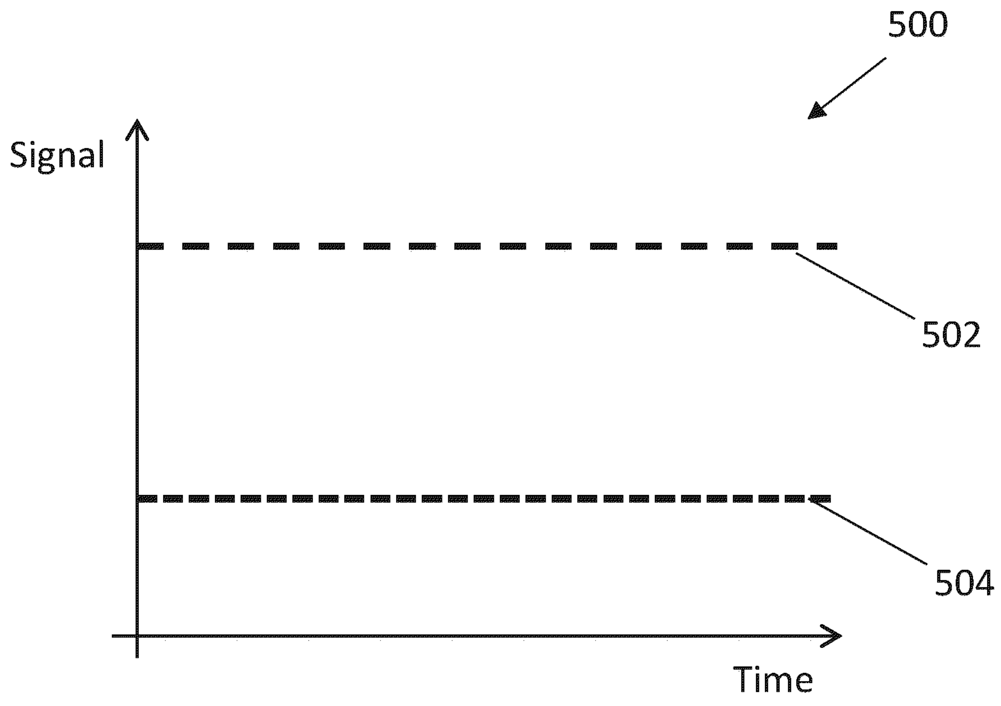
FIG. 4 is a schematic representation of a first composite coagulation waveform according to an embodiment of the invention.

FIG. 4 is a schematic representation of a first composite coagulation waveform 500 according to an embodiment of the invention. The composite waveform 500 comprises a combination of a dominant microwave signal 502 and a supplementary RF signal 504. In particular, the RF signal 504 should be delivered at a power which is low enough to avoid the generation of microplasma at the blade edge which could cause unwanted cutting of tissue. It has been found that by applying a supplementary RF signal 504 at the same time as a microwave signal 502, a greater total power is delivered to biological tissue than when using a microwave signal alone. This results in an increase in the maximum bleeding volume rate that can be coagulated, and so the composite coagulation waveform 500 gives the ability to deal with more severe bleeding than can be stopped using microwave power alone, or by interleaving (e.g. alternating) microwave and RF signals.

For example, the microwave signal 502 may be delivered into biological tissue in a CW mode at a power level of 10 W, and a 400 kHz RF signal 504 may be delivered simultaneously into biological tissue between 75 Vrms and 100 Vrms, which is a suitable level to avoid the generation of microplasma at the blade edge, but enough to result in localised heating to increase energy delivery to biological tissue and improve the rate of coagulation. For example, the power of the RF signal 504 may be less than 10 W, such as 3 W or less, such as 2 W. The RF signal 504 may be adjusted by the generator based on current and/or voltage feedback (such as described above with respect to FIG. 3) in order to control the power delivered to tissue. A composite coagulation waveform 500 configured in this way results in an increase of between 2 W and 20 W of power delivered per millimetre of the active tip in contact with biological tissue.

The actual value of additional power delivered to tissue is dependent on the fluid content of the biological tissue. For example, a higher fluid content will result in increased power delivered to biological tissue, whereas a lower fluid content will result in decreased power delivery. By way of example, the additional power delivered to blood for coagulation in the example described above will be of the order of an additional 7 W of power per millimetre of blade in contact. It will be appreciated that this is a substantial increase relative to the microwave signal 502 power of 10 W.

Figure 5:
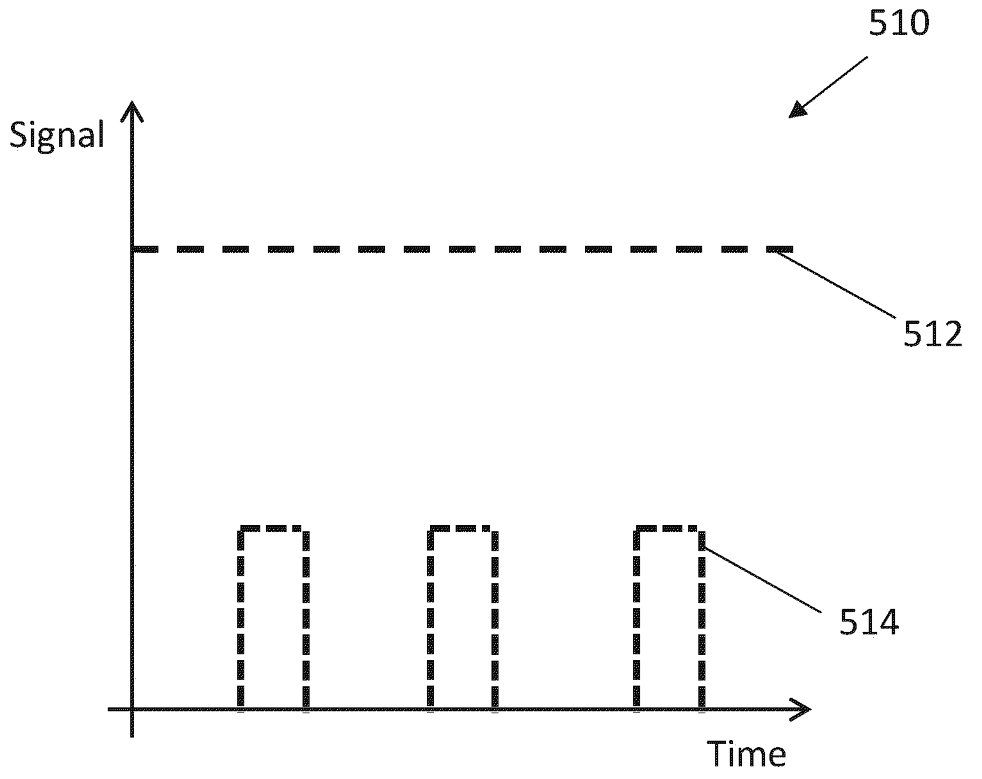
FIG. 5 is a schematic representation of a second composite coagulation waveform according to an embodiment of the invention.

To provide greater control over the power delivered to tissue the RF power may be pulsed. FIG. 5 is a schematic representation of a second composite coagulation waveform 510 according to an embodiment of the invention, wherein the RF signal 514 is pulsed. The microwave signal 512 may be delivered in a continuous wave (CW) manner at a power of 10 W, in substantially the same manner as the microwave signal 502 of the first composite coagulation waveform 500. However, in the second composite coagulation waveform 510, the RF signal 514 is pulsed, with a duty cycle of at least 100 for example. The duty cycle of the RF signal 514 may be controlled by the generator based on current and/or voltage feedback (such as described above with respect to FIG. 3) in order to control the power delivered to tissue. Although the RF signal 514 is shown with rectangular pulses, it will be appreciated that any suitable pulse shape may be chosen according to a desired energy delivery profile.

Figure 6:
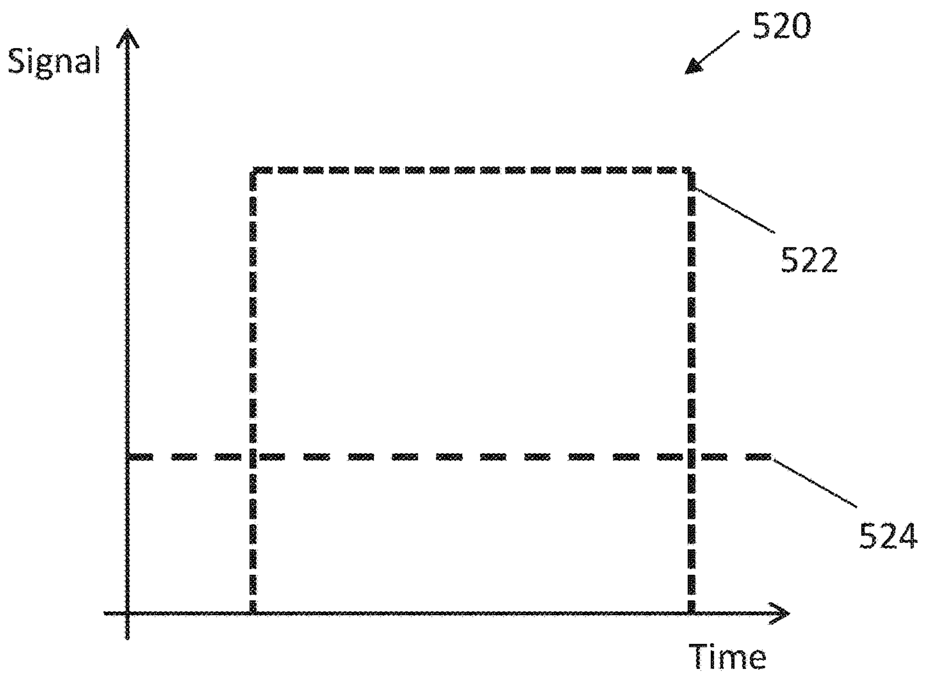
FIG. 6 is a schematic representation of a composite cutting waveform according to an embodiment of the invention.

FIG. 6 is a schematic representation of a composite cutting waveform 520 according to an embodiment of the invention. The composite cutting waveform 520 comprises a combination of a dominant RF signal 522 with a supplementary microwave signal 524. When delivered to a distal tip assembly, for example a bipolar tip as described above with respect to FIG. 2, the RF signal 522 causes extremely high local electric fields between the electrodes, e.g. where contact is made with biological tissue, which causes a microplasma (i.e. a hot thermal plasma) to be formed, which enables cutting of tissue. It has been found that applying a supplementary microwave signal 524 at the same time as the dominant RF signal 522 for cutting increases the power in the microplasma produced by the RF signal 522 and so improves the cutting performance. In addition, the microwave signal 524 may couple to biological tissue, resulting in some denaturing and thereby changing the impedance of the biological tissue to the RF signal. As the microwave signal 524 is delivered at a low level compared with the RF signal 522, any coagulation effect of the microwave signal 524 on tissue is insignificant compared with the cutting provided by the RF signal 522. The cutting composite waveform 520 may be particularly useful during removal of a sessile polyp, or a ribbon cut, for example, where an RF signal alone can become less effective due to the geometry of the polyp, and the impedance presented to the instrument tip by tissue. The supplementary microwave signal 524 increases the power in the microplasma produced by the dominant RF signal 522 to improve cutting performance.

For example, a 400 kHz RF signal 522 may be delivered into biological tissue at 300 Vrms with a power of between 30 W and 40 W, and a microwave signal 524 at a power level of 10 W or less may be simultaneously delivered in a CW mode into the biological tissue to enhance the cutting performance of the RF signal 522. The supplementary microwave signal 524 may be delivered at a power of 10 W or less, for example.

As shown in FIG. 6, the RF signal 522 may be delivered as a pulse. In other examples, the RF signal may be delivered as a plurality of pulses. Although the RF signal 522 is shown as a rectangular pulse, any suitable pulse shape may be chosen according to a desired energy delivery profile. For example, the RF signal 522 may take the form of a pulse having a higher-power cut initiation portion and a lower-power cut sustain portion (for example, as described in GB 2 552 452).

Figure 7:
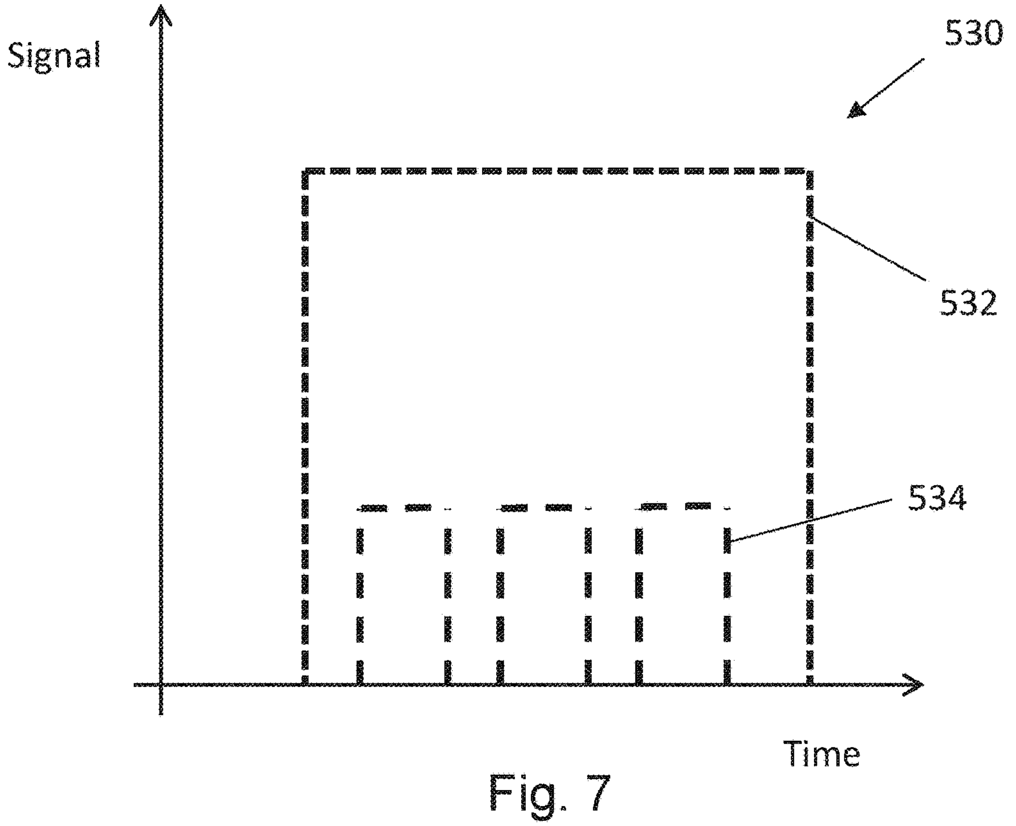
FIG. 7 is a schematic representation of a second composite cutting waveform according to an embodiment of the invention.

To provide greater control over the power delivered to tissue, the microwave signal may not need to be delivered in a CW mode but can be pulsed. FIG. 7 shows an example of a composite cutting waveform 530 according to an embodiment of the invention. In this example, the composite waveform 530 comprises an RF signal 532 substantially the same as shown in FIG. 6 in combination with a microwave signal 534 which is delivered as a series of pulses. For example the microwave signal 534 may be pulsed with a duty cycle of at least 10%. The duty cycle of the microwave signal 534 may be controlled by the generator based on current and/or voltage feedback (such as described above with respect to FIG. 3) in order to control the power delivered to tissue. Although the RF signal 532 and the microwave signal 534 are shown as rectangular pulses, it will be appreciated that any suitable pulse shape may be chosen according to a desired energy delivery profile. In some examples, the RF signal and the microwave signal may be switched synchronously.

In one example of a cutting composite waveform, the dominant RF signal and the supplementary microwave signal may be delivered simultaneously until microplasma have been initiated, whereupon the dominant RF signal may be turned off and the microplasma sustained by the microwave signal alone, with the microwave signal being delivered at the same power or at a higher power.

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

For the avoidance of any doubt, any theoretical explanations provided herein are provided for the purposes of improving the understanding of a reader. The inventors do not wish to be bound by any of these theoretical explanations.

Throughout this specification, including the claims which follow, unless the context requires otherwise, the words "have", "comprise", and "include", and variations such as "having", "comprises", "comprising", and "including" will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment. The term "about" in relation to a numerical value is optional and means, for example, +/−10%.

The words "preferred" and "preferably" are used herein refer to embodiments of the invention that may provide certain benefits under some circumstances. It is to be appreciated, however, that other embodiments may also be preferred under the same or different circumstances. The recitation of one or more preferred embodiments therefore does not mean or imply that other embodiments are not useful, and is not intended to exclude other embodiments from the scope of the disclosure, or from the scope of the claims.

The invention claimed is:

1. An electrosurgical apparatus comprising:

an electrosurgical instrument having a distal tip assembly for delivering radiofrequency (RF) electromagnetic (EM) energy and microwave frequency EM energy into tissue;

an electrosurgical generator arranged to generate radiofrequency (RF) electromagnetic (EM) energy and microwave frequency EM energy; and a feed cable connected to deliver the RF EM energy and the microwave frequency EM energy from the electrosurgical generator to the electrosurgical instrument;

wherein the electrosurgical generator is configured to be operated in each of a coagulation mode and a cutting mode, wherein in the coagulation mode the electrosurgical generator delivers the RF EM energy and the microwave EM energy to the electrosurgical instrument simultaneously in a coagulation composite waveform comprising a high-power microwave signal and a low-power RF signal, wherein in the cutting mode the electrosurgical generator delivers the RF EM energy and the microwave EM energy to the electrosurgical instrument simultaneously in a cutting composite waveform comprising a high-power RF signal and a low-power microwave signal, wherein the low-power microwave signal is delivered from a distal tip at a low power level to denature and desiccate biological tissue, without coagulating biological tissue, and wherein in the coagulation composite waveform the low-power RF signal is delivered from the distal tip at a low power level to result in localized heating of biological tissue without generating microplasmas resulting in tissue cutting.

2. An electrosurgical apparatus according to claim 1, wherein in the coagulation composite waveform the high-power microwave signal is delivered from the distal tip at a high power level to promote coagulation of biological tissue.

3. An electrosurgical apparatus according to claim 1, wherein in the coagulation composite waveform the high-power microwave signal is delivered to the electrosurgical instrument at a power level of 10 W or less.

4. An electrosurgical apparatus according to claim 1, wherein in the coagulation composite waveform the high-power microwave signal is delivered to the electrosurgical instrument as a continuous wave signal.

5. An electrosurgical apparatus according to claim 1, wherein in the coagulation composite waveform the low-power RF signal is delivered to the electrosurgical instrument with a RMS voltage in the range of 75 to 100 V.

6. An electrosurgical apparatus according to claim 1, wherein in the coagulation composite waveform the low-power RF signal is delivered to the electrosurgical instrument as a continuous wave signal, or as a pulsed signal.

7. An electrosurgical apparatus according to claim 1, wherein in the cutting composite waveform the high-power RF signal is delivered from the distal tip at a high power level to generate microplasmas for cutting biological tissue.

8. An electrosurgical apparatus according to claim 1, wherein in the cutting composite waveform the high-power RF signal is delivered to the electrosurgical instrument with an RMS voltage of at least 300 V.

9. An electrosurgical apparatus according to claim 1, wherein in the cutting composite waveform the high-power RF signal is delivered to the electrosurgical instrument as a continuous wave signal, or as a pulsed signal.

10. An electrosurgical apparatus according to claim 1, wherein in the cutting composite waveform the low-power microwave signal is delivered to the electrosurgical instrument at a power level of 10 W or less.

11. An electrosurgical apparatus according to claim 1, wherein in the cutting composite waveform the low-power microwave signal is delivered to the electrosurgical instrument as a continuous wave signal, or as a pulsed signal.

12. A method of delivering radiofrequency (RF) electromagnetic (EM) energy and microwave frequency EM energy from an electrosurgical generator to an electrosurgical instrument that has a distal tip assembly for delivering RF EM energy and microwave frequency EM energy into biological tissue, the method comprising operating the generator to deliver the RF EM energy and the microwave frequency EM energy simultaneously in either of a coagulation composite waveform for promoting haemostasis in biological tissue or a cutting composite waveform for cutting biological tissue, wherein: the electrosurgical generator is configured to operate in a coagulation mode using the coagulation composite waveform and a cutting mode using the cutting composite waveform; the coagulation composite waveform comprises a high-power microwave signal and a low-power RF signal which are delivered simultaneously, the cutting composite waveform comprises a high-power RF signal and a low-power microwave signal which are delivered simultaneously, wherein in the coagulation composite waveform the low-power RF signal is delivered from the distal tip assembly at a low power level to result in localised heating of biological tissue without generating microplasmas resulting in tissue cutting, and wherein in the cutting composite waveform the low-power microwave signal is delivered from the distal tip assembly at a low power level to denature and desiccate biological tissue without coagulating biological tissue.

* * * * *